United States Patent
Hardy et al.

(10) Patent No.: US 7,981,872 B2
(45) Date of Patent: *Jul. 19, 2011

(54) HEMOSTATIC MATERIAL

(75) Inventors: Craig Hardy, Cheshire (GB); Edwin Lee Johnson, Sammamish, WA (US); Paul Luksch, Seattle, WA (US)

(73) Assignee: Medtrade Products Limited, Crewe Business Park, Crewe (GB)

( * ) Notice: Subject to any disclaimer, the term of this patent is extended or adjusted under 35 U.S.C. 154(b) by 251 days.

This patent is subject to a terminal disclaimer.

(21) Appl. No.: 12/159,624

(22) PCT Filed: Dec. 19, 2006

(86) PCT No.: PCT/GB2006/004776
§ 371 (c)(1),
(2), (4) Date: Dec. 2, 2008

(87) PCT Pub. No.: WO2007/074327
PCT Pub. Date: Jul. 5, 2007

(65) Prior Publication Data
US 2009/0149422 A1    Jun. 11, 2009

(30) Foreign Application Priority Data
Dec. 29, 2005  (GB) .................................. 0526505.3

(51) Int. Cl.
*A01N 43/04* (2006.01)
(52) U.S. Cl. ................ 514/55; 514/23; 514/54
(58) Field of Classification Search ........................ None
See application file for complete search history.

(56) References Cited

U.S. PATENT DOCUMENTS

| | | |
|---|---|---|
| 5,420,197 A | 5/1995 | Lorenz et al. |
| 5,538,955 A | 7/1996 | DeRosa et al. |
| 6,806,260 B1 | 10/2004 | Hirofumi et al. |
| 2002/0083955 A1 | 7/2002 | McDevitt et al. |
| 2005/0203058 A1 | 9/2005 | Johnson |
| 2005/0238702 A1 | 10/2005 | Ishihara et al. |

*Primary Examiner* — Patrick Lewis
(74) *Attorney, Agent, or Firm* — Barlow, Josephs & Holmes, Ltd.

(57) ABSTRACT

A hemostatic powder comprises a chitosan salt together with at least one medical surfactant. At least one inert material may optionally be included. The hemostatic powder may be incorporated into wound dressings.

27 Claims, 1 Drawing Sheet

HEMOSTATIC MATERIAL

Figure 1:
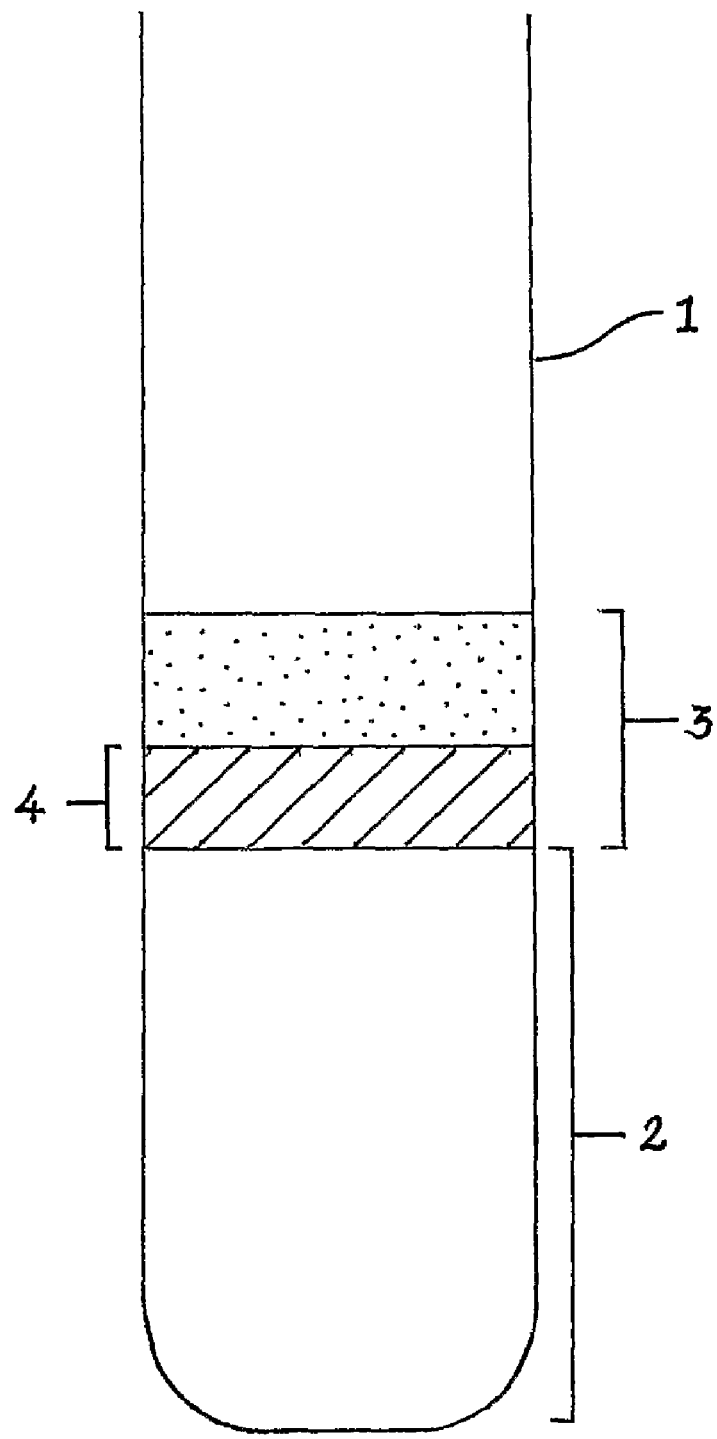

The present invention relates to a hemostatic material for use in controlling bleeding.

Traditionally the primary technique adopted for stemming blood flow is the application of continuous pressure to the wound. This enables clotting factors to collect at the wound site and form a congealed blood mass to stem blood flow. However, this technique is not suitable for severe wounds and wounds having multiple bleeding points. Therefore, bleeding out continues to be a major cause of death.

Death caused by bleeding out is a particular problem on the battlefield. Typically, wounds arising in this situation are accompanied by significant bleeding, and many result in death. Bleeding out is also a significant cause of death amongst the civilian population following trauma.

Attempts have been made to provide products which facilitate the stemming of blood flow from a wound. These include a product sold under the brand name Quick-clot®. Quick-clot® comprises a zeolite compound which absorbs water from the blood flowing from a wound such that the clotting factors present in the blood become concentrated and the blood coagulates more quickly thereby the zeolite and the coagulated blood together form a coagulum to stem blood flow.

Whilst effective Quick-clot® is not without problems. After application to the wound and as the zeolite absorbs water Quick-clot® generates heat. In fact, Quick-clot® quickly reaches temperatures of around 50° C. As it is necessary to apply constant pressure to the wound site following application of Quick-clot® such temperatures make the application of pressure very difficult with medics needing to separate themselves from the wound site with any available material to prevent the discomfort accompanied with the heat generation. Furthermore, as the medic reaches for material to put between himself and the hot wound area he has to release the pressure. This can lead to channels appearing in the developing coagulum through which blood can escape. If this happens then it is necessary to remove Quick-clot® and start again. Ideally, a second person is required to ensure constant compression is applied. Other problems associated with Quick-clot® also relate to the heat generated upon contact with water. For example, as the product is a powder inevitably some settles on the skin surrounding the wound. If the skin is wet the heat generated can cause burns. Using Quick-clot® in wet and windy weather is also problematic as it may cause discomfort or even burns to a person standing nearby.

A further product which comprises chitosan is described in WO 02/102276. The product is a sheet dressing comprising a chitosan layer. The dressing is applied to the site of a wound and forms a seal. The chitosan causes the blood to coagulate which together with the seal formed by the sheet stems the blood flow. However, such products must be applied directly to the source of bleeding, i.e. to an artery. Such application requires skill and accuracy. Military medics and first responders do not have the necessary skills to identify the source of bleeding and apply the dressing thereto. In any event, it would be extremely difficult to perform such a delicate operation on a battlefield or at a trauma site.

GB 2 095 995 and GB 2 129 300 disclose the use of pure chitosan acetate as a hemostatic material. However, the gel which forms from the pure salt is very thin as only the outermost surface of the material is available to act in a short period of time. Quite often this material fails to stop bleeding and even when it does, the clot is very thin and weak so that when the patient is moved, the clot is compromised and bleeding resumes.

Therefore, it is an object of the present invention to provide a hemostatic material which quickly stems the flow of blood from a wound and which is easy and safe to use.

According to the present invention there is provided a hemostatic powder comprising a chitosan salt together with at least one medical surfactant.

Advantageously, the hemostatic powder of the present invention can be applied by a person with only basic training. It is a matter of simply applying the powder to the wound area followed by pressure.

Furthermore, the powder of the present invention does not generate heat following application to the wound site. Therefore, the aforementioned disadvantages of the Quick-clot® product are not seen with the powder of the present invention.

Products which take advantage of biological processes tend to be temperature dependent. Often patients suffering blood loss are either very hot due to exertions on the battlefield or very cold as they have been exposed to cold conditions. Currently available powder products are less effective at such temperature extremes. Advantageously the powder of the present invention is not affected by temperature fluctuations and therefore works equally well at temperatures above and below normal body temperatures (37° C.).

Chitosan is a derivative of solid waste from shell fish processing and can be extracted from fungus culture. Chitosan is a water insoluble cationic polymeric material. Therefore, chitosan for use with the present invention is first converted into a water soluble salt. Therefore, the chitosan salt is soluble in blood to form a gel which stems blood flow.

Chitosan salts are ideally suited for the applications described herein as chitosan is readily broken down in the body. Chitosan is converted to glucosamine by the enzyme lysosyme and is therefore excreted from the body naturally. It is not necessary to remove chitosan from the body.

Furthermore, chitosan salts exhibit mild antibacterial properties and as such their use reduces the risk of infection.

Chitosan salts suitable for use with the present invention include any of the following either alone or in combination: acetate, lactate, succinnate, malate, sulphate, acrylate.

The foregoing examples are provided by way of example only and are not intended to be limiting in any way.

Preferably, the chitosan salt of the present invention is chitosan succinnate.

The chitosan salt is prepared by combining chitosan with the appropriate acid. The acid may be any inorganic or organic acid which yields a soluble chitosan salt. For example, chitosan phosphate is insoluble and so phosphoric acid is unsuitable. The chitosan salt preferably constitutes at least 5% by weight of the powder of the present invention.

Most preferably the chitosan salt constitutes at least 20% by weight of the powder of the present invention.

Suitable medical surfactants for use with the present invention include any of the following either alone or in combination: block copolymers based on ethylene oxide and propylene oxide (e.g. BASF Pluronics®), lauric acid, oleic acid, other fatty acids and fatty acid salts, silicone based surfactants and emulsifiers.

Said medical surfactant preferably constitutes from 0.001 to 10% by weight of the present invention.

Most preferably the medical surfactant constitutes from 0.5 to 1% by weight of the present invention.

Advantageously, the presence of a surfactant gives rise to excellent wetting out properties. The way in which the powder of the present invention wets out is crucial to its performance. That is, if the powder absorbs the blood too quickly the blood and powder simply mix without sufficient gellation having occurred to form a gel clot which is capable of blood flow stemming. On the other hand, if the powder absorbs the blood too slowly gellation occurs in only a small amount of the powder, generally the first few millimeters depth of the powder closest to the wound site. In this case the gel clot which forms is not sufficiently dense to stem the blood flow for a sufficient period of time to allow the patient to be moved to a medical centre. Typically, such a gel clot will break up as the patient is moved and bleeding will resume.

Another factor which has been found to be important to the performance of the powder is the particle size of the chitosan salt. The particle size is measured by the size of sieve which it will go through or is retained by.

Preferably, the chitosan salt has a particle size in the range such that it will pass through a 5 mesh screen but be retained by a 80 mesh screen.

More preferably, the chitosan salt has a particular size in the range such that it will pass through a 20 mesh screen but be retained by a 50 mesh screen.

Most preferably, the particle size of the surfactant will match that of the chitosan salt.

The correct particle size is achieved by grinding the chitosan salt and sorting by any suitable means for example sieving. Such sizing processes are well known to those skilled in the art and will not be described further.

Surprisingly, it has been found that by adding an inert material to the powder i.e. in effect diluting the powder the performance of the powder is actually enhanced. The inert material further enhances the properties of the medical surfactant.

Therefore, the powder of the present invention optionally comprises an inert material.

The inert material may comprise any non-fast gelling hemostat, that is a hemostat that gels within 30 secs to 1 minute of application to a bleeding wound.

Suitable inert materials include any of the following either alone or in combination: chitosan, chitin, cellulose or ground corn meal.

The inert material may be added to the powder in an amount up to 95% by weight of the total composition, typically up to 90% by weight, and more typically up to 80% by weight.

The powder of the present invention preferably has a pH of from 3.5 to 6.0.

The present invention also provides a method of stemming blood flow.

Therefore, according to a second aspect of the present invention there is provided a method of stemming blood flow comprising the steps of: cleaning a wound area where possible; applying to said wound area a hemostatic powder comprising at least one chitosan salt together with at least one medical surfactant; and applying constant pressure to wound area until a gel clot forms.

Constant pressure is preferably applied to the wound area for about 3 minutes.

The powder of the present invention may be incorporated into a chitosan fibre. The fibres may then be used to prepare a wound dressing for superficial non-life threatening bleeding.

Therefore, according to a further aspect of the present invention there is provided a hemostatic powder for use in the manufacture of a hemostatic wound dressing, said powder comprising at least one chitosan salt together with at least one medical surfactant.

According to a still further aspect of the present invention there is provided a hemostatic wound dressing comprising at least one chitosan salt together with at least one medical surfactant.

During the manufacture of the material of the present invention an active base is prepared by preparing a mixture of chitosan and acid in a solvent in which the chitosan is insoluble (usually 80:20 ethanol:water). Where used a surfactant may also be added to this mixture. The solvent is evaporated to provide a substantially dry active base material. The active base material is then combined with other materials such as inert materials to provide the powder of the present invention.

The invention will now be described further by way of example only with reference to the following examples and figures:

FIG. 1 is a diagrammatic representation of the penetrability test described herein.

FIG. 1 shows a rest tube 1 comprising an aqueous layer 2 and a layer of hemostatic powder 3. The distance traveled by the aqueous layer 2 is shown as band 4.

EXAMPLE 1

Powder Process

The ethanol (or any other solvent in which chitosan will not dissolve) and the water are mixed. The acid is dissolved in the ethanol and water combination. The surfactant is dissolved in the same solution.

The raw chitosan powder is added to the solution and mixed in a dough style mixer for 15 minutes.

The resulting slurry is dried at 60° C. to remove the ethanol and water.

The resulting solids are passed through a grinding mill to produce the required particle size.

This chitosan salt can then be mixed and blended with the dry inert powder to produce the final hemostat.

EXAMPLE 2

Fibre Coating

A solution of chitosan in water with the required acid is made. Surfactants and or plastiziers can be added.

This can then be applied to an existing fabric such as gauze by spraying or coating etc.

The resulting fabric is then dried.

A final texturising process can be used to soften the fabric.

EXAMPLE 3

Chitosan Fabric

The ethanol (or any other solvent in which chitosan will not dissolve) and the water are mixed. The acid is dissolved in the ethanol and water combination. The surfactant/plasticiser is dissolved in the same solution.

The resulting solution can be applied to a fibre or a fabric made of the fibres or a blend of chitosan fibres with any other fibre.

The resulting wet fibre mass is dried to remove the ethanol and water.

If necessary a final texturising process can be used to soften any resulting fabric.

Table 1 shows some of the various blends prepared and their hemostatic efficacy and penetrability.

The 'Active Base 15' is prepared by forming a pre-mix of 59% chitosan and 41% succinic acid in an 80:20 ethanol:water solution. The solvent is then removed by drying at 60° C.

TABLE 1

| Active Base 15 | Insoluble Chitosan | Chitin | Corn meal | Calcium Alginate | Aquasorb A400 CMC | Hemostitic efficacy (mls required) | Penetrability (height cm) |
|---|---|---|---|---|---|---|---|
| 100 | — | — | — | — | — | 0.15 | 0.3 |
| 50 | 50 | — | — | — | — | 0.2 | 1.5 |
| 50 | — | 5 | — | — | — | 0.2 | 2.5 |
| 25 | — | 75 | — | — | — | 0.35 | 3.0 |
| 50 | — | — | 5 | — | — | 0.25 | 3.0 |
| 50 | — | — | — | 50 | — | 0.2 | 3.0 |
| 25 | — | — | — | 75 | — | 0.4 | 3.0 |
| 75 | — | — | — | 25 | — | 0.2 | 2.5 |
| 50 | — | — | — | — | 50 | 0.3 | 2.5 |

The hemostatic efficacy and penetrability properties of the present invention were determined by the following tests:

Penetrability 5 mls of distilled water were added to a test tube. A drop of red food dye was added to the water. 3 g of hemostatic powder were gently tipped on top of the water such that a layer was formed (see FIG. 1).

After 1 minute the distance traveled by the water into the hemostatic powder was measured.

The sample was monitored for gel blocking.

A distance of 0.5 cm or more indicates an effective hemostat for the purposes of the present invention.

Hemostatic Efficacy

The ability of a hemostat to bond with particles like bentonite is a measure of its hemostatic efficacy.

To a container containing 30 ml of distilled water was added 0.5 g of hemostatic powder. The mixture was stirred moderately for 3 minutes using a magnetic stirring bar and stirrer. The stirred mixture was then filtered through a Whatman #1 filter paper.

The amount of filtrate required to flocculate 50 ml of a settled 0.5% Bentonite® solution was determined.

The use of less than 1 ml of the filtrate indicates an effective hemostat for the purposes of the present invention.

The following table 2 shows various active base compositions, together with the results of the penetrability and hemostatic efficacy tests:

TABLE 2

| Sample | Chitosan | Succinic Acid | Surfactant | Penetrability Test (Height cm) | Hemostatic efficacy (mls required) |
|---|---|---|---|---|---|
| A | 58.93 | 41.07 | None | 1.5 | 0.25 |
| B | 58.93 | 41.07 | None | 1.4 | 0.25 |
| C | 58.90 | 41.04 | 0.06 lauric acid | 3.5 | 0.15 |
| D | 58.59 | 40.83 | 0.58 Pluronic F58 | 3.3 | 0.15 |

It is of course to be understood that the present invention is not intended to be restricted to the foregoing examples which are described by way of example only.

The invention claimed is:

1. A hemostatic powder comprising a chitosan salt together with at least one medical surfactant.

2. A hemostatic powder according to claim 1, wherein the chitosan salt comprises one or more of the group consisting of: chitosan acetate, chitosan lactate, chitosan succinnate, chitosan malate, chitosan sulphate, chitosan acrylate.

3. A hemostatic powder according to claim 2, wherein the chitosan salt comprises chitosan succinnate.

4. A hemostatic powder according to claim 1, wherein the chitosan salt constitutes at least 5% by weight of the hemostatic powder.

5. A hemostatic powder according to claim 4, wherein the chitosan salt constitutes at least 20% by weight of the hemostatic powder.

6. A hemostatic powder according to claim 1, wherein the at least one medical surfactant comprises one or more of the group consisting of: block copolymers based on ethylene oxide and propylene oxide, fatty acids, fatty acid salts, silicone based surfactants and emulsifiers.

7. A hemostatic powder according to claim 6, wherein the at least one medical surfactant is a fatty acid selected from lauric acid and oleic acid.

8. A hemostatic powder according to claim 1, wherein the at least one medical surfactant constitutes from 0.001 to 10% by weight of the hemostatic powder.

9. A hemostatic powder according claim 8, wherein the at least one medical surfactant constitutes from 0.5 to 1% by weight of the hemostatic powder.

10. A hemostatic powder according to claim 1, wherein the chitosan salt comprises particles that will pass through a 5 mesh screen but be retained by a 80 mesh screen.

11. A hemostatic powder according to claim 10, wherein the chitosan salt comprises particles that will pass through a 20 mesh screen but be retained by a 50 mesh screen.

12. A hemostatic powder according to claim 1, wherein the particle size of the chitosan salt and the particle size of the at least one medical surfactant are substantially equivalent.

13. A hemostatic powder according to claim 1, wherein the hemostatic powder further comprises at least one inert material.

14. A hemostatic powder according to claim 13, wherein the at least one inert material comprises one or more of the group consisting of:
chitosan, chitin, cellulose, ground corn meal.

15. A hemostatic powder according to claim 13, wherein the inert material constitutes up to 95% by weight of the hemostatic powder.

16. A hemostatic powder according to claim 15, wherein the inert material constitutes up to 90% by weight of the hemostatic powder.

17. A hemostatic powder according to claim 16, wherein the inert material constitutes up to 80% by weight of the hemostatic powder.

18. A hemostatic powder according to claim 1, wherein the hemostatic powder has a pH of from 3.5 to 6.

19. A hemostatic powder according to claim 1 for use in the manufacture of a hemostatic wound dressing.

20. A hemostatic wound dressing comprising a hemostatic powder according to claim 1.

21. A hemostatic wound dressing according to claim 20, wherein the hemostatic wound dressing comprises fibres.

22. A hemostatic wound dressing according to claim 21, wherein the fibres are chitosan fibres.

23. A method of manufacturing a hemostatic powder, comprising the steps of:

preparing a mixture of chitosan and an acid in a solvent in which the chitosan is insoluble, evaporating the solvent, and mixing the resulting chitosan salt with at least one medical surfactant.

24. A method according to claim 23, wherein the solvent is 80:20 ethanol:water.

25. A method according to claim 23 either of claim 23, wherein the method includes the step of adding at least one inert material.

26. A method of stemming blood flow, including the steps of: applying to a wound area a hemostatic powder according to claim 1; and applying constant pressure to the wound area until a gel clot forms.

27. A method according to claim 26, wherein the step of applying constant pressure to the wound area is carried out for at least 3 minutes.

* * * * *